(12) United States Patent
Coupier

(10) Patent No.: US 9,879,217 B2
(45) Date of Patent: Jan. 30, 2018

(54) CRYOPRESERVATION BAGS AND METHOD OF USE THEREOF FOR CLOSED SYSTEM, HIGH CAPACITY CELL-BANKING

(71) Applicant: Merial Inc., Duluth, GA (US)

(72) Inventor: Hervé François Coupier, Orliénas (FR)

(73) Assignee: MERIAL, INC., Duluth, GA (US)

( * ) Notice: Subject to any disclaimer, the term of this patent is extended or adjusted under 35 U.S.C. 154(b) by 0 days.

(21) Appl. No.: 14/826,720

(22) Filed: Aug. 14, 2015

(65) Prior Publication Data
US 2016/0369225 A1   Dec. 22, 2016

Related U.S. Application Data

(60) Provisional application No. 62/037,181, filed on Aug. 14, 2014.

(51) Int. Cl.
  *C12M 1/00*   (2006.01)
  *C12M 3/00*   (2006.01)
  (Continued)

(52) U.S. Cl.
  CPC ........... *C12M 45/22* (2013.01); *A01N 1/0268* (2013.01); *A61J 1/10* (2013.01); *B01L 3/505* (2013.01);
  (Continued)

(58) Field of Classification Search
  CPC ...... C12M 23/14; C12M 41/12; C12M 23/26; A01N 1/0236; A01N 1/021; A01N 1/02
  See application file for complete search history.

(56) References Cited

U.S. PATENT DOCUMENTS 5,863,715 A * 1/1999 Rajotte ............... A01N 1/0284
                                                   165/263
6,022,344 A   2/2000 Meijer et al.
(Continued)

FOREIGN PATENT DOCUMENTS

WO   WO 04/108057 A2   12/2004
WO   WO 2006/069389 A1   6/2006
(Continued)

OTHER PUBLICATIONS

Heidemann et al. A new seed-train expansion method for recombinant mammalian cell lines. Cytotechnology 38: 99-108, 2002. Cited in ISR.
(Continued)

*Primary Examiner* — Nathan Bowers
(74) *Attorney, Agent, or Firm* — Judy Jarecki-Black; Chad Kitchen; Merial, Inc.

(57) ABSTRACT

The disclosure provides a cell freezing and storage bag assembly and a method for using the assembly in banking eukaryotic cells for later seed train expansion. The bag is constructed principally of fluorinated ethylene propylene (FEP) fabric, and is designed to be filled such that the cell suspension has a very thin cross-section. The bag design includes at least an inlet conduit and an outlet or inoculation conduit, which can be sterilely welded to the source of the eukaryotic cells. The use of at least two sterile-weldable conduits allows for "closed system" filling of the bags, which significantly reduces the risk of contamination relative to other cell-banking methods. The bag also include a sleeve, which can be thermo-welded to form an enclosure, which protects the inlet and outlet conduits against contamination and mechanical damage during freezing, storage and subsequent thawing. In the method, once each bag is filled, its corresponding inlet conduit is sealed, and both the inlet and outlet conduits are enclosed within the bag's sleeve. This closed system method obviates the need for sterile environments (e.g. laminar flow unit).

10 Claims, 5 Drawing Sheets

(51) Int. Cl.
*A01N 1/02* (2006.01)
*B01L 3/00* (2006.01)
*B01L 9/00* (2006.01)
*C12M 1/12* (2006.01)
*C12M 1/34* (2006.01)
*A61J 1/10* (2006.01)
*A61J 1/14* (2006.01)

(52) U.S. Cl.
CPC ............... *B01L 9/00* (2013.01); *C12M 23/14* (2013.01); *C12M 23/26* (2013.01); *C12M 37/00* (2013.01); *C12M 37/02* (2013.01); *C12M 37/04* (2013.01); *C12M 41/44* (2013.01); *A61J 1/1462* (2013.01); *A61J 1/1475* (2013.01); *B01L 2300/021* (2013.01); *B01L 2300/0681* (2013.01); *B01L 2300/0809* (2013.01); *B01L 2300/1894* (2013.01)

(56) References Cited

U.S. PATENT DOCUMENTS

| | | | |
|---|---|---|---|
| 6,123,696 A * | 9/2000 | Coelho | A61J 1/10 206/219 |
| 6,183,460 B1 | 2/2001 | Smith et al. | |
| 6,670,175 B2 | 12/2003 | Wang et al. | |
| 6,786,054 B2 | 9/2004 | Voute et al. | |
| 7,618,584 B2 | 11/2009 | Lampeter et al. | |
| 8,028,532 B2 | 10/2011 | Voute et al. | |
| 8,177,123 B2 | 5/2012 | Voute et al. | |
| 8,448,457 B2 | 5/2013 | Cutting et al. | |
| 2006/0166364 A1 | 7/2006 | Senesac | |
| 2006/0167401 A1 | 7/2006 | Cohen | |

FOREIGN PATENT DOCUMENTS

| | | |
|---|---|---|
| WO | WO 2010/119311 A1 | 10/2010 |
| WO | WO 2011/140076 A1 | 11/2011 |
| WO | WO 2C/176630 A1 | 12/2012 |
| WO | WO 2D/033720 A1 | 3/2013 |

OTHER PUBLICATIONS

Seth et al. Development of a New Bioprocess Scheme Using Frozen Seed Train Intermediates to Initate CHO Cell Culture Manufacturing Campaigns. Biotech. and Bioeng. vol. 110, No. 5, May 2013. Cited in ISR.

Anonymous: "KryoSure (R) Cryopreservation Bags" Jul. 23, 2013 https://web.archive.org/web/20130723092645/http://americanfluoroseal.com/products/kryosure-cryopreservation-products. Cited in ISR.

* cited by examiner

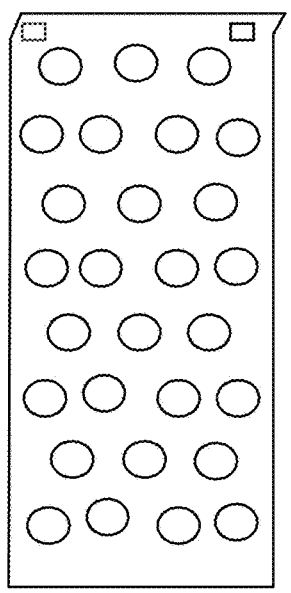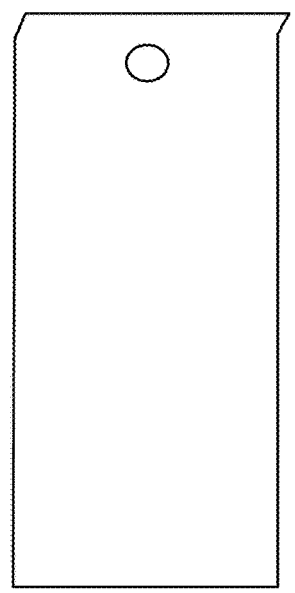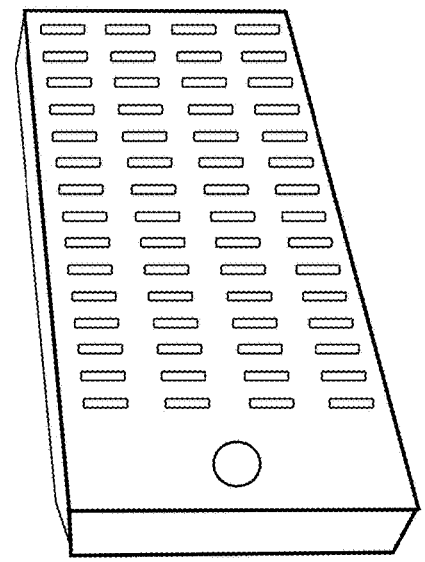
Fig. 2A          Fig. 2B

CRYOPRESERVATION BAGS AND METHOD OF USE THEREOF FOR CLOSED SYSTEM, HIGH CAPACITY CELL-BANKING

CROSS-REFERENCE TO OTHER APPLICATIONS

This application claims priority to US provisional application number U.S. Ser. No. 62/037,181, filed on 14 Aug. 2015, and herein incorporated by reference in its entirety.

FIELD OF THE INVENTION

The present invention relates to a flexible cryopreservation bag assembly and method for the freezing, storing, and transferring of eukaryotic cells, including mammalian, avian and insect cells. These cells are used to inoculate a bioreactor.

BACKGROUND OF THE INVENTION

Biotechnology products, including recombinant viral vectors, typically involve introducing some genetic modification into eukaryotic cells and then growing these cells in a bioreactor or in multiple large cell culture dishes or vessels. Other important products include virus vaccine strains and modified live viruses.

For the production of a recombinant viral vectors, virus vaccine strains, and modified live viruses, a uniform cell source is needed to inoculate bioreactors or cell culture vessels. Typical cell sources include specific lines of genetically modified eukaryotic cells and controlled cell clones having cGMP status. This provides a basis for a Manufacturer's Working Cell Bank (MWCB). An MWCB consists of many aliquots (portions) of a cell suspension, each containing the same type of cells and approximately the same number of cells. These aliquots are prepared on the same day and frozen at the same time. The aliquots are then kept at very cold temperatures (cryopreserved). For each run, one or more of these aliquots of cells is thawed to provide the same starting point as any other run with the same cells.

Successful inoculation of a bioreactor or cell culture vessels with eukaryotic cells requires a minimum cell density to achieve proper cell growth. If the cell density is below the minimum level, additional time is required to achieve commercial cell growth levels, which adds expense to the process and increases the opportunity for contaminants to enter the cell environment. If the cell density is too high, the nutrients in the media can be depleted, which may result in reduced cell growth, lower cell productivity and possibly death of the cell culture.

OTHER REFERENCES

U.S. Pat. No. 6,670,175 (to Bayer Pharmaceuticals) discloses and claims polytetrafluoroethylene (PTFE) cryopreservation bags, whereas the disclosure provides fluorinated ethylene propylene (FEP) bags and a method for using the bags in a closed system cell banking scheme. FEP is a copolymer of hexafluoropropylene and tetrafluoroethylene. It differs from the PTFE resins in part, in that it is melt-processible using conventional injection molding and screw extrusion techniques. Fluorinated ethylene propylene was invented by DuPont and is sold under the brand name Teflon® FEP. Other brand names are NEOFLON® from Daikin or DYNEON® FEP from Dyneon/3M.

U.S. Pat. No. 8,177,123 (to Sartorius Stedim) discloses systems and methods for freezing, storing and thawing biopharmaceutical materials.

WO 2006/078796 A2 (Michael Cohen) discloses an apparatus and method for stem cell preservation and usage.

Yet despite the foregoing and other efforts in the field, the risk of contamination during filling, thawing and emptying of freezer bags remains a critical challenge. Accordingly, apparatuses and methods are required to reduce the risk of contamination and to better control cryopreservation, relative to current cell-banking approaches.

SUMMARY OF THE INVENTION

Currently, the lead time for cell amplification is unacceptably long and there are too many open phases during the filling and draining steps. To solve this problem, the instant disclosure provides is a novel cell freezing and storage bag assembly and method for using the assembly in cryobanking eukaryotic cells for later seed train expansion. The bag is constructed principally of fluorinated ethylene propylene (FEP) fabric. The bag is designed to be filled to a fraction of its maximum capacity so that the cell suspension has a very thin cross-section. The bag design includes at least an inlet conduit and an outlet or inoculation conduit, which can be sterilely welded to the source of the eukaryotic cells. The use of at least two sterile-weldable conduits allows for "closed system" filling of the bags, which significantly reduces the risk of contamination relative to other cell-banking methods.

The bag also includes a sleeve, which can be thermo-welded to form an enclosure, which protects the inlet and outlet conduits against contamination and mechanical damage (PVC is brittle at low temperatures) during freezing, storage and subsequent thawing. In the method, once each bag is filled, its corresponding inlet conduit is sealed, and both the inlet and outlet conduits are enclosed within the bag's sleeve. The sleeve is separate from the enclosure containing the cells and may receive label. Because the sleeve is closed, it avoids contact between outlet conduit and water from the water-bath at thawing, decreasing the risk of contamination. During inoculation, the contents of the bag are drained via a sterile-weldable outlet conduit or inoculation line. Protective "openwork" cassettes allow for optimal thermal transfer between the outside environment (e.g. water-bath or liquid nitrogen) and the cell aliquots.

BRIEF DESCRIPTION OF THE DRAWINGS

The accompanying drawings incorporated in and forming a part of the specification illustrate several aspects of the present inventions, and together with the description serve to explain the principles of the inventions. The components of the drawings are not necessarily to scale, emphasis instead being upon clearly illustrating principles of the present inventions.

FIG. 2A presents a front view (left) and rear view (right) of a protective metal cassette, which encloses the bags during freezing, storage and thawing;

FIG. 2B presents another example of the cassettes, in its closed position;

DETAILED DESCRIPTION OF THE INVENTION

Figure 1A:
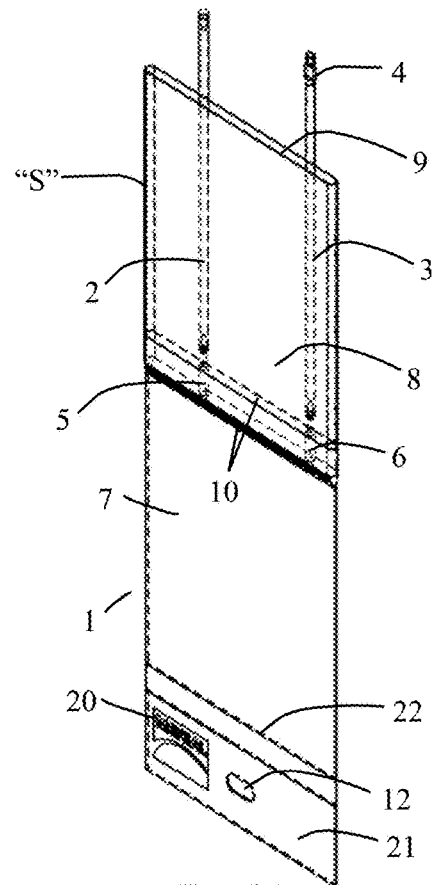
FIG. 1A is a drawing of a particular embodiment of the cryopreservation bag.

As used herein, the term "batch culture" refers to a cell culturing technique in which a quantity of fresh culture medium is inoculated with cells that rapidly enter a logarithmic growth phase and in which the growth medium of the culture is not continuously removed and replaced with fresh medium.

As used herein, the term "fed batch culture" refers to a cell culturing technique in which a quantity of fresh culture medium is inoculated with cells initially, and additional culture nutrients are fed (continuously or in discrete increments) to the culture during the culturing process, with or without periodic cell and/or product harvest before termination of culture.

As used herein, the term "perfusion culture" refers to a cell culturing technique in which a quantity of fresh medium is inoculated with cells that rapidly enter a logarithmic growth phase (as above) and in which the growth medium is continuously removed from a culture and replaced with fresh medium.

As used herein, the term "bioreactor" shall refer to a vessel for culturing cells.

In one embodiment, the bioreactor is a "flexible bag bioreactor". A "flexible bag bioreactor" is a sterile chamber capable of receiving a liquid media and which additionally comprises connectors, ports, adaptors and flexible tubing. In one embodiment, the chamber is made of plastic. In a specific embodiment, the chamber is made of multilayered laminated clear plastic. In a further specific embodiment, the chamber is made of multilayer laminated clear plastic and has a fluid contact layer made of FEP.

Additionally, the connectors, ports, and adaptors may be made from any kind of plastic including but not limited to: polyethylene, polypropylene, and polycarbonate while the tubing may be constructed from any kind of plastic including but not limited to: thermoplastic elastomer or silicone (e.g. platinum-cured silicone).

Appropriate "flexible bag bioreactor" chambers can be commonly found in the art and include, but are not limited to, those described in U.S. Pat. No. 6,544,788, which is herein incorporated by reference in its entirety.

As used herein, "fluorinated ethylene propylene (FEP) fabric" refers to a flexible material that resembles a film or cloth made by any means from FEP. Fluorinated ethylene propylene was invented by DuPont and is sold under the brand name Teflon® FEP. Other brand names are NEOFLON® from Daikin or DYNEON® FEP from Dyneon/3M. Saint-Gobain also provides similar bag/fabric combinations.

The "inlet conduit" is a flexible tube through which cells are added to the cryopreservation bags prior to freezing and storage. Polyvinyl chloride is a preferred material for both the inlet and outlet conduits. Similarly, the "outlet conduit" is a flexible tube through which cells leave the cryopreservation bags subsequent to thawing.

When cell freezing bags of the present invention are used, they will be placed on their side in a metal cassette (also referred to as a box or canister) in a substantially level orientation. The cell suspension thickness at any point within a bag should not exceed approximately 10 or 11 millimeters. If cell suspension thickness are substantially more than 10 or 11 millimeters, the cells adjacent to the bag surface will experience different freezing and thawing conditions than cells at the interior of the suspension, and may react differently over the course of freezing and thawing and when subsequently used in a bioreactor. The term "thin cross section" refers to the foregoing dimensions.

Cell freezing and storage bag assembly: The assembly includes the cell freezing bag and associated tubing, ports and interconnects.

As used herein, the term "cryopreservation" refers to a process by which cells, tissues, or any other substances susceptible to damage caused by time or by enzymatic or chemical activity are preserved by cooling and storing them to sub-zero temperatures.

As used herein, the term "cryobanking" refers to a technique by which cells are mixed with a cryoprotectant (e.g. DMSO with or without hydroxyethyl starch (HES)) and placed in a container appropriate for storage under cryopreservation conditions. These containers are then frozen using techniques well known in the art and stored at low temperatures, typically between about $-130°$ C. and about $-196°$ C. The collection of cells obtained by the process is a cell bank.

As used herein, the term "master cell bank" shall refer to a culture of cells (e.g. fully characterized cells) that have been grown from a single clone, dispensed into storage containers (e.g. dispensed into the containers in a single operation), and stored under cryopreservation conditions as described above. In certain embodiments, the cells are suitable for later use in a production cell culture and a further harvest of the therapeutically relevant proteins and/or viruses, including viruses, produced thereby.

As used herein, the term "cryobag" is a sterile chamber that is capable of receiving a liquid medium, is appropriate for cold storage between about $-130°$ C. and about $-196°$ C., and may additionally comprise connectors, ports, adaptors and flexible tubing. As described herein, the cryobag is ideally constructed of Fluorinated Ethylene Propylene (FEP).

As used herein, the term "shake flask" shall refer to a vessel used as a culture flask in which the medium is constantly agitated during incubation.

As used herein, the term "shake flask seed train" shall refer to a method of cell expansion in which an aliquot of cells is first cultured (seeded) in a shake flask and grown therein. The cells are cultured according to their growth rate and are usually split into larger and/or multiple vessels during their growth until the biomass has reached a level sufficient to inoculate a bioreactor.

As used herein, the term "seed density" shall refer to the initial cell density at which a flask or bioreactor is inoculated.

As used herein, the term "therapeutically relevant protein" shall refer to any protein that may be used to create a treatment for a disease or disorder or to treat a disease or disorder in an animal, including mammals such as mice, rats, monkeys, apes, and humans. These proteins may include, but are not limited to, binding polypeptides such as monoclonal antibodies, Fc fusion proteins, anticoagulants, blood factors, bone morphogenetic proteins, engineered protein scaffolds, enzymes, growth factors, hormones, interferons, interleukins, and thrombolytics.

Accordingly, in a preferred embodiment, the invention provides a cell freezing and storage bag that supports a new method for a closed phase cell-banking system.

In an embodiment, the bag is constructed principally of FEP. The bag is designed to hold enough cells that a bioreactor or cell culture vessels can be inoculated directly from its contents. The bag is designed to be filled to a fraction of its maximum capacity so that when placed on its side, the cell suspension has a very thin cross-section. The bag design includes a transfer set that can be sterilely welded to the source of the eukaryotic cells. The bag design includes at least an inlet conduit and an outlet or inoculation conduit, which can be sterilely welded to the source of the eukaryotic cells. The use of at least two sterile-weldable conduits allows for "closed system" filling and draining of the bags, which significantly reduces the risk of contamination relative to other cell-banking methods.

The bag also include a sleeve, which can be thermo-welded to form an enclosure, which protects the inlet and outlet conduits against contamination and mechanical damage during freezing, storage and subsequent thawing. In the method, once each bag is filled, its corresponding inlet conduit is sealed, and both the inlet and outlet conduits are enclosed within the bag's sleeve. The sleeve is separate from the enclosure containing the cells, such that it does not interfere with thermal transfer. During inoculation, the contents of the bag are drained via a sterile-weldable outlet conduit or inoculation line.

The cell freezing bag of the present invention is made of a FEP fabric in place of EVA and PFE (prior art bags). FEP fabric is flexible at minus 196° C. (the temperature of liquid $N_2$). Because of its flexibility at low temperature, and in turn the reduced possibility of low temperature fracture, this fabric feature provides additional protection to the contents of the cell freezing bag during freezing, long-term storage, and thawing.

The cell freezing bag is designed to hold up to 400 mL of cell suspension, 400 times the volume typically frozen in screw top vials. Volumes from as little as a several milliliters up to at least about 400 mL, or even larger volumes, are also possible using the disclosed cryopreservation bag design. The cell densities are comparable for the new cell freezing bags and the vials that are currently used. Because of this volume difference, the bags can hold approximately 100 (or up to about 400) times more cells than the vials. A single cell freezing bag contains enough cells to allow direct inoculation of a bioreactor or another suitable cell culture vessel. Several bags may be used to inoculate very large vessels.

The cell suspension volumes to be frozen are a fraction of the cell freezing bag potential capacity. This limits the thickness of the cell suspension. Because the cell suspension is thin, heat transfer is rapid and the cells can be frozen and thawed uniformly at an optimal rate. Uniform freezing and thawing help ensure the homogeneity of the cells.

The cell freezing bags are to be manufactured with an integral inlet conduit and outlet or inoculation conduit. The conduits are composed of lengths of flexible tubing, and most particularly made of PVC. When the bags are to be filled, the inlet conduit is sterilely welded to a length of tubing that is in fluid communication with the source of the cell suspension. Sterile welding devices and methods are well-known to those skilled in the art of preserving cells or other biological materials. This "closed system" procedure virtually eliminates the chance of contamination when the bags are filled and drained.

Each leg of the transfer set is connected to the cell freezing bag. Each leg has a pinch clamp or similar device to control the flow of cells to the attached cell freezing bag. The transfer set and attached bags are sterilized and delivered as a unit. For each bag the filling sequence is:

a) the inlet conduit is sterilely welded to a one leg, which is in fluid communication with a source of cells;

b) the pinch clamp on the attached transfer set leg is opened;

c) the cell suspension is pumped into the bag via its inlet conduit;

d) the pinch clamp is closed;

e) the inlet conduit is thermo-sealed, f) the bag is cut above the seal made in e), disconnecting the bag from the transfer set without having exposed its contents to the outside air (i.e. closed phase);

g) the inlet and outlet conduit are withdrawn inside the bag's sleeve, and the bag is placed inside a protective metal casing, which will be used to house the bag during freezing and storage (this step is useful when a plurality of bags must be processed);

h) the bag is temporarily removed from its protective casing, and its sleeve is sterilely thermo-sealed to produce a new compartment, which encloses the inlet and outlet conduits. The enclosure protects the inlet and outlet conduits from direct exposure to liquid N2 and water baths;

i) the metal case is now closed around the filled and sealed bag, and lowered to the appropriate storage temperature.

If the cell suspension is pumped at a constant rate, the bags can be filled based on a fixed time interval. Once the inlet conduit is sealed and cut, the transfer set is no longer attached to the bag. This eliminates one of the points of vulnerability during storage.

This invention uses an outlet conduit for draining the bags contents. This conduit remains sterilely sealed during filling, freezing, storage and thawing of the bag. The outlet conduit may alternatively be referred to as an inoculation line. One end of the inoculation line is attached to the body of the cell freezing bag. This attached end communicates freely with the compartment that contains the cell suspension. During storage, the inoculation line is protected from mechanical damage by being tightly enclosed (along with the sealed inlet conduit) in a compartment (i.e. the enclosure formed when the bag's sleeve is thermo-sealed in step (h) above. When the contents of the bag are to be used, the free end of the inoculation line is sterilely welded to a length of tubing that is connected to the inoculation bioreactor or cell culture vessels.

Accordingly, the invention encompasses a new method for the seed train expansion of eukaryotic cells. Under this new method, the number of cells in each aliquot of the Manufacturer's Working Cell Bank (MWCB) is increased. This reduces the extent to which cells must be multiplied in the seed train expansion. It is also possible to increase the number of cells per aliquot by concentrating them (see for example US 2014/0273206, to Genzyme). Applicant envisions that a combination of both the instant high volume, closed phase cell-banking method, combined with a concentration method, would be extremely advantageous.

In one embodiment, the invention provides a high capacity, closed phase, cryopreservation cell banking system, comprising:

a. a user interface for controlling and monitoring the dispensing of liquid biological materials into a plurality of cryopreservation bags;

b. a plurality of cryopreservation bags, comprised of at least two sterile-weldable fluid conduits;

c. a plurality of fluid connections, adapted to fill the plurality of bags;
d. a thermo-sealing means, for sealing tubing and bags;
e. a plurality of metal cassettes for containing, freezing, storing & thawing the bags.

In a particular embodiment, the bags are made principally or entirely of fluorinated ethylene propylene (FEP) and the conduits are made principally or entirely of polyvinyl chloride (PVC). In one embodiment, the bags consist of one inlet and one conduit.

In another embodiment, the bags comprise a sleeve, into which the fluid conduits may be sealed, after the bags have been filled with biological materials, to prevent contamination of the biological materials, and to prevent mechanical damage to the fluid conduits, during freezing, storage and thawing.

In one embodiment, the high capacity cryopreservation bag comprises:
  a. a first fluorinated ethylene propylene (FEP) enclosure;
  b. at least one rigid FEP inlet conduit, in fluid connection with the first enclosure, and connectable to a first flexible PVC tubing;
  c. at least one rigid FEP outlet conduit, in fluid connection with the first enclosure, and connectable to a second flexible PVC tubing; and
  d. an FEP pouch, which is initially open at one end, and which is contiguous with the first enclosure, but thermosealed therefrom, and encircling both the rigid inlet conduit and the rigid outlet conduit, such that the pouch is neither in fluid communication with the first enclosure, nor the inlet nor outlet ports; and wherein the pouch extends sufficiently far enough such that when the first enclosure has been filled with the biological material, the PVC tubes may be withdrawn into the pouch, which is then thermosealed to form a second enclosure, which now contains both PVC tubes.

In an embodiment, the second enclosure of the cryopreservation bag contains a sleeve or other means for receiving and containing a label, which may be used to recite information about the bag's contents.

In another embodiment, the rigid FEP inlet conduit is connected to the inlet flexible PVC tubing via a rigid plastic barb-type taper connector; and, the rigid FEP outlet conduit is connected to the outlet flexible tubing via a rigid plastic barb-type connector. In this embodiment, each connector is tapered on both sides such that they can fit tightly inside their respective conduits.

In an embodiment, the conduits are encircled by retaining rings.

In another embodiment, the second enclosure protects the PVC tubes against damage and contamination that can occur during freezing, storing or thawing of the bag.

In an embodiment, the bag has been filled with the biological material and the PVC tubes have been withdrawn into the thermosealed second enclosure. The filled bag is now ready to be subjected to lowered temperatures, down to the appropriate storage temperature (e.g. liquid $N_2$). In an embodiment, the second enclosure contains a label.

In an embodiment, the invention provides a cryopreservation bag cassette, which is adapted to contain a cryopreservation bag according to the instant disclosure. The cassette contains and protects the bag during freezing, storage and thawing.

In an embodiment, the invention provides a closed system process for banking large volumes of cells comprising the following steps:

a. connecting the high capacity bag according to the disclosure to the high capacity closed banking system of the disclosure;
b. bringing a source of cells into fluid connection with the system;
c. allowing the cells to come into fluid contact with the bags and to fill each bag to a desired capacity;
d. aseptically thermo-sealing each of the inlet PVC tubes;
e. withdrawing both the inlet tubing and the outlet tubing into each bag's pouch;
f. thermo-sealing each pouch to enclose and protect the PVC tubes and the labeling;
g. placing the bags into the cassettes; and
h. freezing the bags within their respective cassettes thereby banking the large volumes of cells.

In an embodiment, the invention provides a closed system method for thawing and dispensing cells banked according to the instant disclosure, comprising the following steps:
  a. exposing each sealed bag to a water bath containing water at a suitable thawing temperature;
  b. cutting the thermo-sealed enclosure to allow access to the outlet or inoculation conduit (as this is a closed system, laminar flow cabinet conditions are not required);
  c. sterilely welding the inoculation conduit to tubing, which is in conditional fluid communication with a target bag, vessel or bioreactor;
  d. draining each bag into the target bag, vessel or bioreactor; thereby thawing and dispensing the banked cells.

In an embodiment, a dedicated inoculation bioreactor may be directly inoculated by sterilely transferring the contents of the cell freezing bag to the bioreactor or other appropriate cell culture vessels. This inoculation may take place without any intervening tissue culture-flasks, roller bottles, shake flasks, or comparable vessels. The initial volume of the culture in the dedicated inoculation bioreactor may be, for example, 2 L, increasing to 15 L as the cells multiply. Accordingly, with a common cell concentration of $150 \times 10^6$/ml, and bag capacity of 400 mL, it is possible to seed a 200 L vessel directly at a common cell seeding concentration of about $0.3 \times 10^6$/ml.

In an embodiment, the closed phase, cell-banking system may be used to freeze and store any one of the following: prokaryotic cells, eukaryotic cell lines, modified cell lines, cell lines harboring recombinant viral vector, concentrated antigens (e.g. inactivated FMD virus or virions) and DNA vaccines.

In one embodiment, the cells are mammalian cells. In another embodiment, the mammalian cells are selected from the group consisting of: CHO, CHO-10-DBX11, CHODG44, CHO-S, CHO-K1, Vero, BHK, HeLa, COS, MDCK, HEK-293, NIH-3T3, W138, BT483, Ils578T, HTB2, BT20, T47D, NSO, CRL7030, HsS78Bst cells, PER.C6, SP2/0-Ag14, and hybridoma cells. Insect cells as Sf9 might also be a target for Merial In another embodiment, the cells are stably transfected or transduced cells.

EXAMPLES

Example 1

Figure 1B:
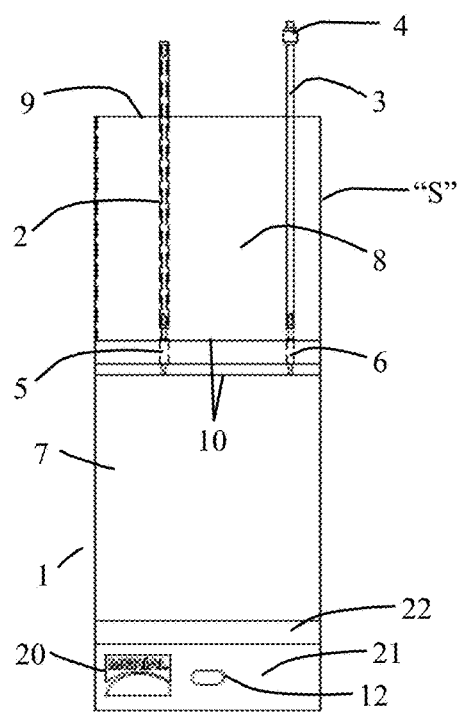
FIG. 1B is a drawing of another view of the cryopreservation bag.

FIG. 1 depicts a bag according to the instant disclosure. Shown in FIGS. 1A and 1B are an FEP bag (1); a first PVC conduit (2); a second PVC conduit (3); and an optional porous filter, to allow for a gas (e.g. ethylene oxide) sterilization process (4). The inlet conduit (2) and outlet conduit (3) both remain sterilely fixed to the rigid inlet conduit (5) and rigid outlet conduit (6) throughout the filling, freezing, storage and thawing steps. And while the currently depicted rigid conduits are of the spike port variety, the cryopreservation bag may also employ FEP barb ear stubs.

As shown in FIG. 1, the bag has a first fluorinated ethylene propylene (FEP) enclosure (7), which is adapted to aseptically receive and contain a volume of biological materials (e.g. cells). The first enclosure (7) is in fluid connection with a rigid FEP inlet conduit (5), which is connectable to a first flexible PVC tubing (2). The first enclosure is also in fluid connection with a rigid FEP outlet conduit (6), which is connectable to a second flexible PVC tubing (3). The bag also includes an FEP pouch (8), which is initially open at one end (9), and which is otherwise contiguous with enclosure (7), but not fluidly connected therewith owing to a seal (10) between enclosure (7) and pouch (8). The rigid conduits (5, 6) are thus sealably engaged with, and encircled by, the FEP that makes up the enclosure (7) and pouch (8), and the pouch (8) is neither in fluid communication with the first enclosure, nor the inlet (5) nor outlet (6) ports.

Figure 1C:
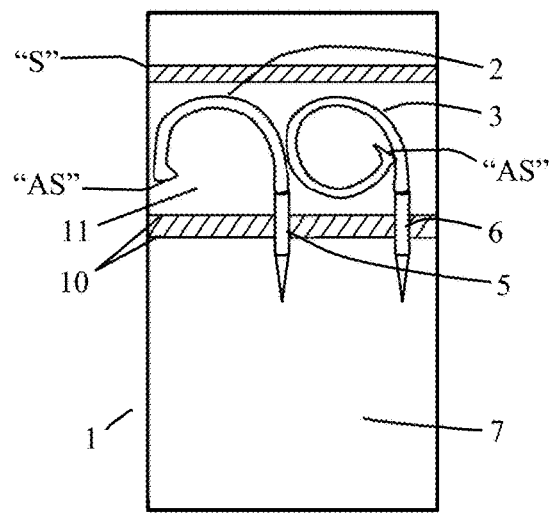
FIG. 1C is a picture of an actual cryopreservation bag, made according to the disclosure, with its sleeve sealed to enclose the inlet and outlet conduits.
Figure 3A:
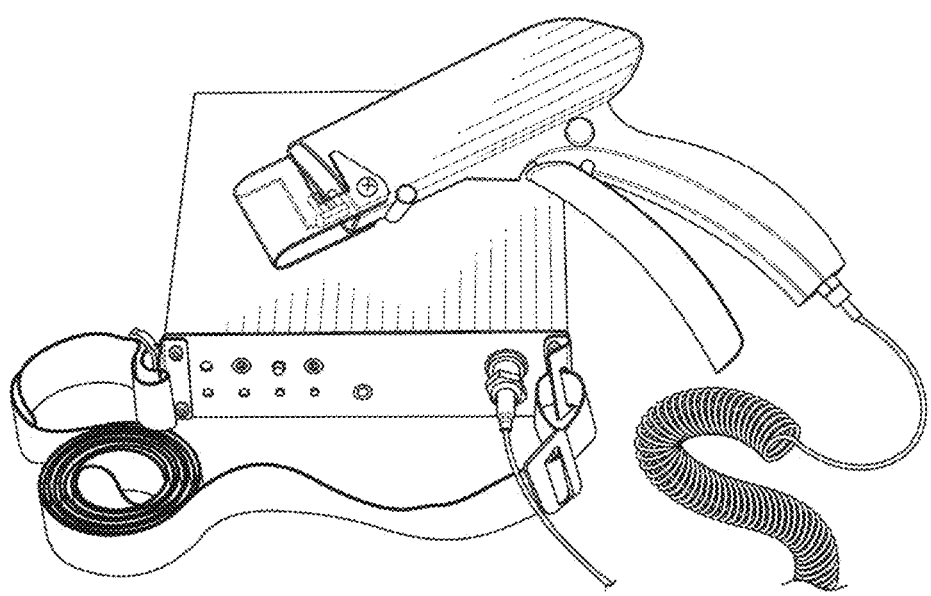
FIG. 3A is a picture of a typical hand-held thermo-welder.
Figure 3B:
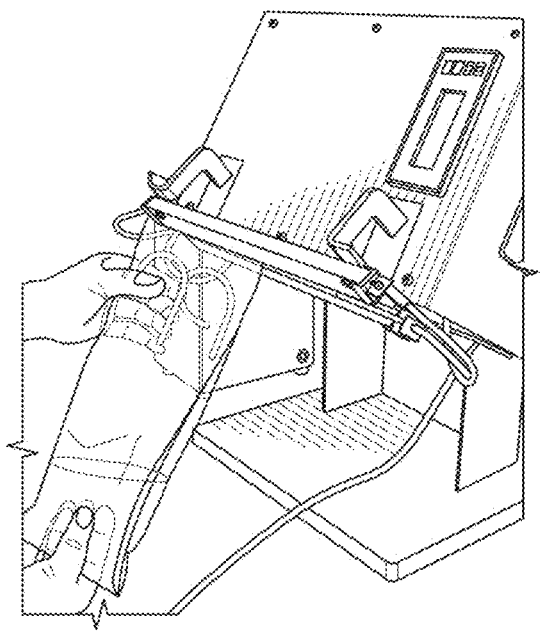
FIG. 3B is a picture of a table-top sealer, which may be employed to seal cryopreservation bags.
Figure 3C:
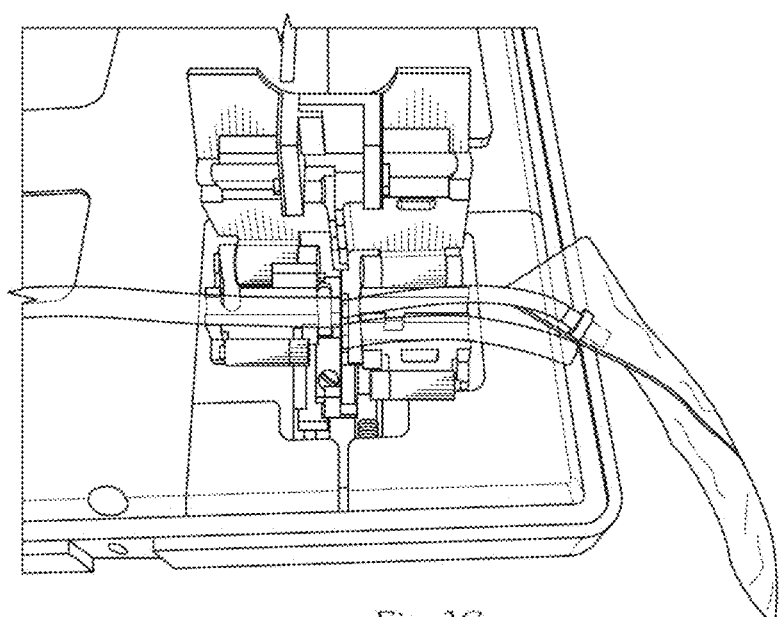
FIG. 3C is a picture of a thermo-welding device, which aseptically joins plastic tubing (e.g. inlet and outlet conduits)
Figure 4:
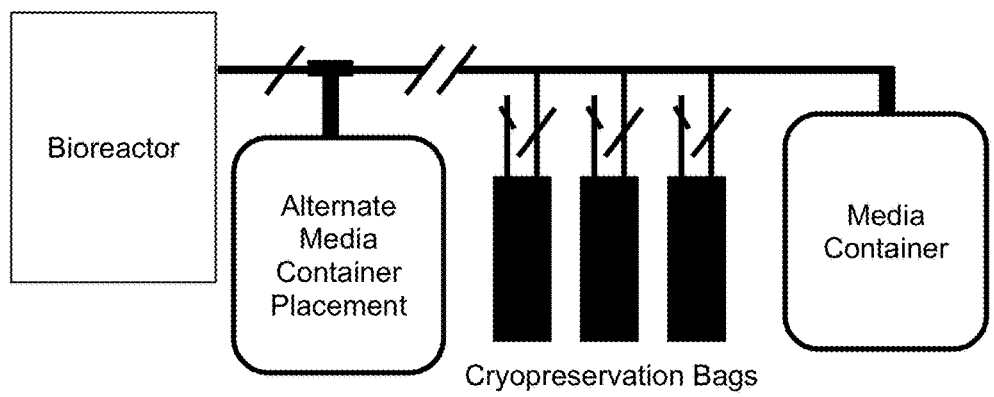
FIG. 4 is a schematic drawing depicting thawed bags being inoculated into a bioreactor.

As shown in FIGS. 1A and 1B, the pouch (8) extends sufficiently far enough such that when the first enclosure (7) has been filled with the biological material, the PVC tubes may be withdrawn into the pouch (see FIG. 1C), which is then thermosealed at a point approximately indicated by the letter "S," to form a second enclosure (ii), which now contains both PVC tubes (2, 3), which have themselves been aseptically sealed (marked in FIG. 1C with the letters "AS"). The bag (1) also contains an orifice (12), which is suitable for receiving a means for hanging the bag (e.g. to facilitate filling and emptying of biological material from the bags). Any suitable label (20) may be imprinted on the bag (1), and ideally, should be located in the portion (21) of the bag that contains the hanging orifice (12). This portion (21) is sealably separated from the rest of the bag by a thermoseal (22) between it and enclosure (7).

What is claimed is:

1. A high capacity, closed, cryopreservation cell banking system, comprising:
   a. a user interface for controlling and monitoring the dispensing of liquid biological materials into a plurality of high capacity, liquid nitrogen temperature resistant cryopreservation bags;
   b. a plurality of cryopreservation bags, each bag comprising:
      i. a first fluorinated ethylene propylene (FEP) enclosure;
      ii. at least two sterile-weldable fluid conduits and adapted for use in a high capacity biological material, closed cryopreservation banking system;
      iii. a first rigid FEP inlet conduit, in fluid connection with the first FEP enclosure, and connectable to the first of the two sterile-weldable fluid conduits, wherein said first conduit is a first flexible PVC tube;
      iv. a second rigid FEP outlet conduit, in fluid connection with the first FEP enclosure, and connectable to the second of the two sterile-weldable fluid conduits, wherein said second conduit is a second flexible PVC tube; and
      v. a FEP pouch, which is initially open at one end, and which is contiguous with the first FEP enclosure, but thermosealed therefrom, and encircling both the rigid inlet conduit and the rigid outlet conduit, such that the pouch is neither in fluid communication with the first enclosure, nor the inlet nor outlet ports; and wherein the pouch extends sufficiently far enough such that when the first enclosure has been filled with the biological material, the PVC tubes may be withdrawn into the pouch, which is then thermosealed to form a second enclosure, which now contains both PVC tubes;
   c. a plurality of fluid connections, adapted to fill the plurality of bags;
   d. a thermo-sealing means, for sealing the sterile-weldable fluid conduits and bags; and
   e. a plurality of cassettes for containing, freezing, storing & thawing the bags.

2. The system of claim 1, wherein the second enclosure of the bag contains a sleeve or other means for receiving and containing a label, which may be used to recite information about the bag's contents.

3. The system of claim 1, wherein the rigid FEP inlet conduit is connected to the inlet flexible PVC tubing via a rigid plastic barb-type taper connector, and wherein the rigid FEP outlet conduit is connected to the outlet flexible tubing via a rigid plastic barb-type connector, each connector tapered on both sides such that they can fit tightly inside their respective conduits and PVC tubing.

4. The system of claim 2, wherein the conduits further comprise retaining rings.

5. The system of claim 2, wherein the second enclosure protects the PVC tubes against damage and contamination that can occur during freezing, storing or thawing of the bag.

6. The system of claim 1, wherein the bag has been filled with the biological material and wherein the PVC tubes have been withdrawn into the thermosealed second enclosure.

7. The system of claim 6, wherein the second enclosure further contains a label.

8. The system of claim 1, wherein each cryopreservation bag further comprises:
   a. a porous filter, affixed to and in fluid communication with the bag's second PVC tube, which tube is fluidly connected to the bag's rigid FEB outlet conduit, said filter allowing for gas sterilization of the bag; and
   b. an orifice, which is suitable for receiving a hangar for hanging the bag;
   wherein the first and second PVC tubes both remain sterilely fixed to the rigid inlet and outlet conduits, respectively, when the bag is being filled, frozen, stored or thawed.

9. A closed system process for banking large volumes of cells using the system of claim 1, comprising the following steps:
   a. connecting the high capacity bag(s) to the high capacity closed banking system;
   b. bringing a source of cells into fluid connection with the system;
   c. allowing the cells to come into fluid contact with the bags and to fill each bag to a desired capacity;
   d. aseptically thermo-sealing each of the inlet PVC tubes;
   e. withdrawing both the inlet tubing and the outlet tubing into each pouch;
   f. thermo-sealing each pouch to enclose and protect the PVC tubes and the labeling;
   g. placing the bags into the cassettes; and
   h. freezing the bags within their respective cassettes thereby banking the large volumes of cells.

10. The process of claim 9, further comprising the following steps:
   a. exposing each sealed bag to a water bath containing water at a suitable thawing temperature;

b. cutting the thermo-sealed enclosure to allow access to the outlet or inoculation conduit;
c. sterilely welding the inoculation conduit to tubing, which is in conditional fluid communication with a target bag, vessel or bioreactor;
d. draining each bag into the target bag, vessel or bioreactor; thereby thawing and dispensing the banked cells.

* * * * *